United States Patent
Mo et al.

(10) Patent No.: US 6,577,967 B2
(45) Date of Patent: Jun. 10, 2003

(54) AUTOMATIC ADJUSTMENT OF VELOCITY SCALE AND PULSE REPETITION FREQUENCY FOR DOPPLER ULTRASOUND SPECTROGRAMS

(75) Inventors: Larry Y. L. Mo, Waukesha, WI (US); Lihong Pan, Brookfield, WI (US); Richard M. Kulakowski, Richfield, WI (US); Michael J. Washburn, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/994,212

(22) Filed: Nov. 26, 2001

(65) Prior Publication Data
US 2002/0116141 A1 Aug. 22, 2002

Related U.S. Application Data

(63) Continuation of application No. 09/224,633, filed on Dec. 31, 1998.

(51) Int. Cl.⁷ .......................... G06F 19/00; G01R 23/10
(52) U.S. Cl. ..................................................... 702/76
(58) Field of Search ............................... 702/39, 76, 77, 702/100, 120, 189; 600/441, 450, 455, 456; 73/861, 25

(56) References Cited

U.S. PATENT DOCUMENTS

| | | | | |
|---|---|---|---|---|
| 4,476,874 A | * | 10/1984 | Taenzer et al. | 600/441 |
| 4,713,971 A | * | 12/1987 | Johannes | 70/861.25 |
| 5,313,947 A | * | 5/1994 | Micco | 600/455 |
| 5,349,524 A | * | 9/1994 | Daft et al. | 600/441 |
| 5,501,224 A | * | 3/1996 | Shiki | 600/456 |
| 5,564,424 A | * | 10/1996 | Yao | 600/455 |
| 5,633,809 A | * | 5/1997 | Wissenbach et al. | 702/45 |
| 5,654,509 A | * | 8/1997 | Miele et al. | 70/602 |
| 5,676,148 A | * | 10/1997 | Koo et al. | 600/447 |
| 5,777,892 A | * | 7/1998 | Nabity et al. | 702/143 |
| 5,891,040 A | * | 4/1999 | Grenon et al. | 600/455 |
| 5,931,784 A | * | 8/1999 | Kajiwara et al. | 600/441 |
| 6,023,977 A | * | 2/2000 | Langdon et al. | 73/629 |
| 6,126,601 A | * | 10/2000 | Gilling | 600/440 |
| 6,142,943 A | * | 11/2000 | Mo et al. | 600/447 |
| 6,146,331 A | * | 11/2000 | Wong | 600/454 |
| 6,176,143 B1 | * | 1/2001 | Mo et al. | 73/861.25 |
| 6,177,923 B1 | * | 1/2001 | Arenson et al. | 345/589 |

* cited by examiner

Primary Examiner—John Barlow
Assistant Examiner—Demetrius Pretlow
(74) Attorney, Agent, or Firm—McAndrews, Held & Malloy, Ltd.; Peter J. Vogel; Michael A. Dellapenna (57) ABSTRACT

An ultrasound transmitter generates ultrasound signals at an adjustable pulse repetition rate. A Doppler unit generates Doppler signals from ultrasound backscattered signals and stores them in a memory. A logic unit performs an algorithm which automatically adjusts the polarity and position of the velocity scale of a display and automatically adjusts the pule repetition rate of the transmitter based on analysis of the signals.

30 Claims, 6 Drawing Sheets

AUTOMATIC ADJUSTMENT OF VELOCITY SCALE AND PULSE REPETITION FREQUENCY FOR DOPPLER ULTRASOUND SPECTROGRAMS

CROSS-REFERENCE TO RELATED APPLICATIONS

This is a continuation of application Ser. No. 09/224,633, filed Dec. 31, 1998.

STATEMENT REGARDING FEDERALLY SPONSORED RESEARCH OR DEVELOPMENT

Not applicable.

BACKGROUND OF THE INVENTION

This invention relates to ultrasonic diagnostic systems which measure the velocity of fluid flow using spectral Doppler techniques. In particular, the invention relates to automatic adjustment of velocity scale and pulse repetition frequency for such systems.

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers, such as blood cells. This frequency shift translates into the velocity of the blood flow.

In state-of-the-art ultrasonic scanners, the pulsed or continuous wave (CW) Doppler waveform is computed and displayed by a video processor in real-time as a gray-scale spectrogram of velocity versus time with the gray-scale intensity (or color) modulated by the spectral power. The data for each spectral line comprises a multiplicity of frequency data bins for different frequency intervals, the spectral power data in each bin for a respective spectral line being displayed in a respective pixel of a respective column of pixels on the display monitor. Each spectral line represents an instantaneous measurement of blood flow.

Each vertical line in the spectral display corresponds to a Doppler frequency spectrum at a given time instant. Positive Doppler frequencies correspond to flow towards the transducer, and negative frequencies correspond to flow away from transducer. The Doppler shift limits are +/−PRF/2, where PRF is the pulse repetition frequency, or the sampling frequency of the Doppler signal. Given the Doppler beam to vessel angle (which is specified by the user via a Doppler angle cursor graphic over the B-mode image), the Doppler frequency shifts can be converted into velocity units according to the standard Doppler equation.

In practice, over the FFT analysis time interval, the velocity distribution within the pulsed Doppler sample volume in a vessel can be positive or negative depending on the flow direction with respect to the transducer. If the Doppler spectrogram display is inverted because the flow is all negative, the user can press an invert key to invert the Doppler spectral lines, such that −PRF/2 maps to the top of the spectrogram display.

Aliasing occurs when the pulse repetition frequency (PRF) is below the Nyquist rate of the random Doppler signal, and for example results in the positive frequency spectrum being wrapped around to the negative frequency axis. Provided that the total spectral bandwidth is less than PRF, a simple shift of the baseline, $f_{shift}$ can effectively unwrap the spectrum. In conventional Doppler scanners, such baseline shifts are usually effected by the operator via a toggle switch on the front panel. Often this will require the user to toggle the baseline shift key a few times depending on the $f_{shift}$ step size.

If the spectrum bandwidth is larger than PRF, however, it can not be unwrapped simply by adjusting the polarity or baseline position of the velocity scale. In that case, the user must increase the PRF thereby extending the limits of the velocity scale via a front-panel control switch. On the other hand, if the spectrum bandwidth is much smaller than the current PRF setting, the user will usually reduce the PRF to expand the height of the spectrogram in the display area.

Typical clinical Doppler exams can be time-consuming since they involve adjustment of a variety of control keys and switches for sample volume size, flow direction cursor angle, velocity limits (PRF), baseline shift and invert, auto max/mean velocity trace etc. As a result, there is a need for automating some of these basic Doppler adjustments in order to improve both the speed and reliability of the Doppler exam.

BRIEF SUMMARY OF THE INVENTION

The preferred embodiment of the invention is useful in an ultrasound system comprising a Doppler image display unit for displaying a Doppler image with an adjustable polarity and an adjustable position along the frequency axis. The embodiment improves the appearance of the Doppler image by transmitting ultrasound waves at a predetermined pulse repetition frequency, preferably by an ultrasound transmitter unit. Doppler signals are generated in response to the ultrasound waves backscattered from a subject under study, preferably by an ultrasound receiver unit. Memory signals having memory values are stored. The memory signals include first signals having first values representing the magnitudes of at least some of the component frequencies of the Doppler signals generated over a predetermined time period in response to the backscattered ultrasound waves due to fluid flow in a first direction and second signals having second values representing the magnitudes of at least some of the component frequencies of the Doppler signals generated over the predetermined time period in response to the backscattered ultrasound waves due to fluid flow in a second direction opposite the first direction. The storing preferably is accomplished in a digital memory. A third signal having a third value related to a noise signal level present in the system is generated. The memory values are analyzed based at least in part on the third value, preferably by a logic unit. One or more of the polarity, position and pulse repetition frequency (PRF) may be adjusted in response to the analyzing whereby the Doppler image generated by the Doppler image display unit is changed.

By using the foregoing methods and apparatus, the polarity and position of a Doppler image are automatically adjusted and the PRF is automatically adjusted, thereby aiding the reading and interpretation of the Doppler image. For example, if the spectrum is aliased, it will be automatically unwrapped via baseline shift and/or an increase in PRF. If the spectrum is inverted, it can be automatically inverted back for an upright display. If the spectrum bandwidth is too small relative the current PRF or velocity limits, the PRF is automatically reduced for optimal display. These automated velocity scale and PRF adjustments improve the ease-of-use of the Doppler equipment, and ultimately the speed and reliability of the Doppler exam.

DETAILED DESCRIPTION OF THE INVENTION

Figure 1:
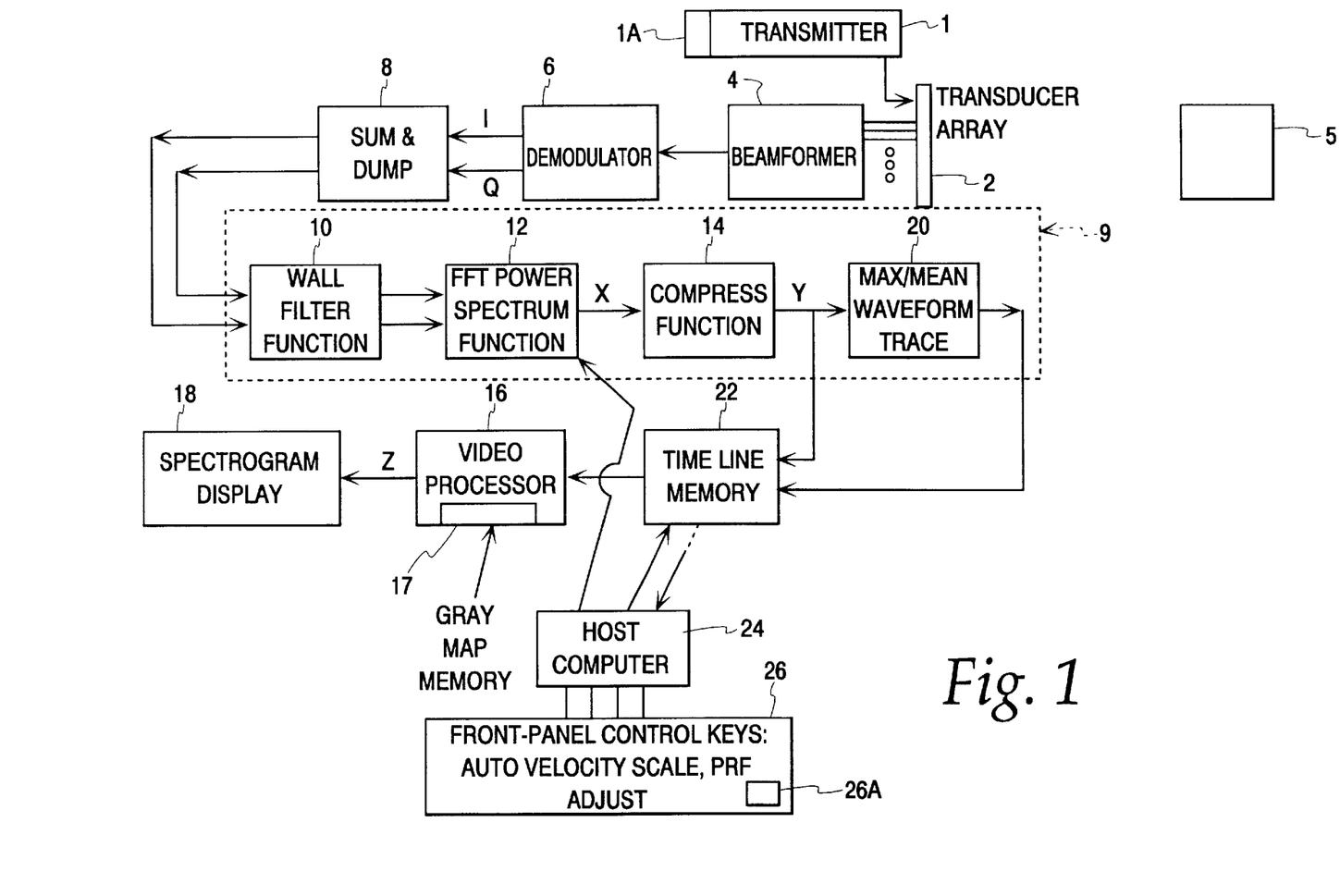
FIG. 1 is a schematic block diagram showing the signal processing chain for a preferred spectral Doppler mode of an ultrasound imaging system made in accordance with the invention. I and Q denote the in-phase and quadrature components of the demodulated signal, respectively.

Referring to FIG. 1, a transmitter unit 1 energizes an ultrasound transducer array 2 to transmit ultrasound bursts which are fired repeatedly at a pulse repetition frequency (PRF) so that ultrasound waves are backscattered from a predetermined portion or volume of a patient or subject under study. An exemplary transmitter unit is shown in U.S. Pat. No. 5,349,524 (Daft et al.) which is incorporated by reference and is commonly assigned. The transmitter unit includes a control 1A for adjusting the PRF which is typically in the kilohertz range. Alternatively, the array 2 may be continuously energized.

The return RF signals are detected by the transducer elements and then formed into a receive beam by a receive beamformer 4. For a digital system, the summed RF signal from each firing is demodulated by a demodulator 6 into its in-phase and quadrature (I/Q) components. The I/Q components are integrated (summed) over a specific time interval and then sampled by block 8. The summing interval and transmit burst length together define the length of the sample volume as specified by the user. The "sum and dump" operation effectively yields the Doppler signal corresponding to the ultrasound signal backscattered from the sample volume in the patient.

The Doppler signal is transmitted to a midprocessor 9 which comprises a logic unit, such as a digital signal processor (DSP). Alternatively, a microprocessor, microsequencer or microcontroller may be employed. Hardwired logic units also can be utilized to perform the operations described in connection with the DSP.

The Doppler signal is assessed by the DSP through a digital wall filter function 10 which rejects any clutter in the signal corresponding to stationary or very slow moving tissue. The filtered signals are used by the DSP to perform an FFT power spectrum function or algorithm 12 which typically takes Fast Fourier Transforms (FFT's) over a moving time window of 64 to 128 samples. Function 12 generates frequency signals having values representing the magnitudes of at least some of the Doppler component frequencies represented by the output of wall filter function 10.

Figure 2:
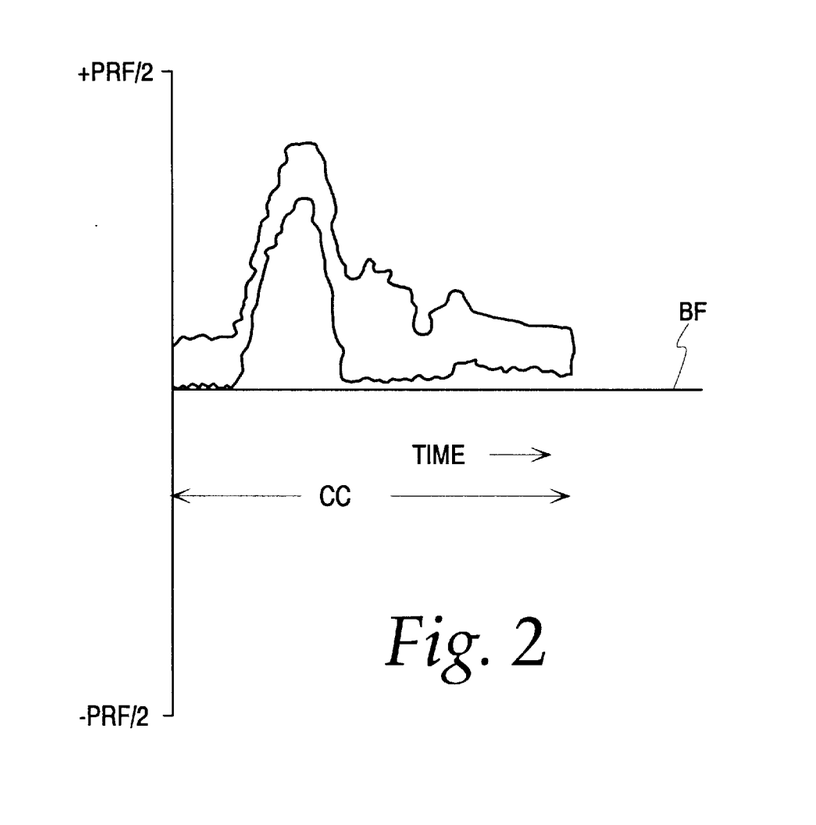
FIG. 2 is a graph showing a typical Doppler image created on a display unit.

Each FFT power spectrum is compressed by the DSP in a compressor function 14 and the resulting signals are stored in a time line memory (TLM) 22. The signals from memory 22 are mapped by a video processor 16 to a gray scale map for display on monitor 18 as a single spectral line at a particular time point in the Doppler velocity (frequency) versus time spectrogram. The data for the spectral line is stored in a time line memory 22. The gray scale map is stored in a memory 17 within the video processor 16. FIG. 2 shows a typical Doppler image on display 18.

Doppler waveform tracing is performed by processing block 20 after the FFT power spectrum X is compressed in accordance with a compression function h(x)=y.

A host logic unit 24, such as a computer, microprocessor, microsequencer, microcontroller or hard wired circuits for conducting logic operations, communicates with the DSP in midprocessor 9, video processor 16 and time line memory 22. A user communicates with computer 24 via front panel control keys, including a key (not shown) for inverting the image on display 18 and shifting the frequency baseline of display 18.

Figure 1A:
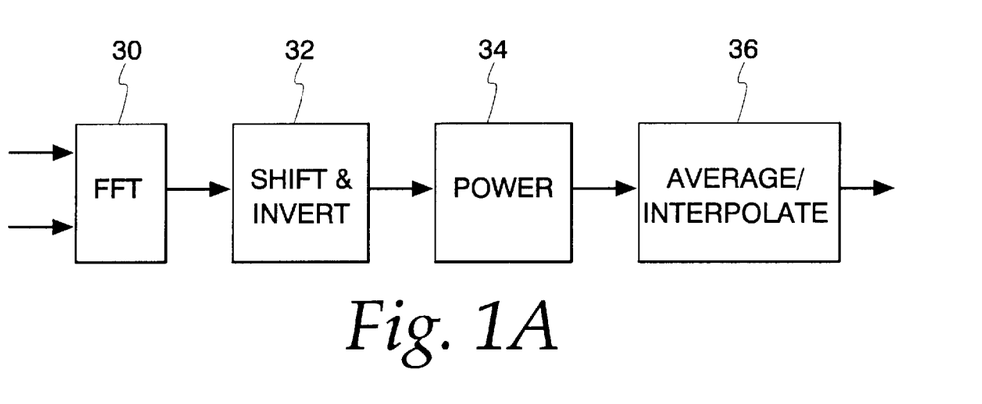
FIG. 1A is a schematic block diagram of a portion 12 of the system shown in FIG. 1.

FIG. 1A shows the key computations involved in FFT power spectrum function 12 which generates the individual spectral lines with the selected polarity and frequency baseline in the spectogram display 18. Central to this is the FFT operation 30 which transforms windowed I/Q data segments to the frequency domain.

The frequency domain signals are shifted and/or inverted in operation 32. This operation results in an inversion or vertical shifting of the Doppler image on display 18. Operation 34 takes the absolute magnitude squared of the signals produced by operation 32 to generate power spectrum signals. In operation 36, the power spectrum signals are averaged, and/or interpolated to fill up the TLM. The magnitude of the resulting power spectra signals are compressed via a logarithmic function 14 (FIG. 1) for the video display 18 which typically has 6–8 bits of gray map resolution. The maximum/mean frequency waveform of the compressed spectrum can be traced out over time and superposed (not shown) on spectrogram display 18.

The preferred embodiment of the present invention uses a precise model of the probability distribution of X to establish a threshold as a reference for automatically adjusting velocity scale and pulse repetition frequency. It is well established (see Mo et al., "'Speckle' in continuous wave Doppler ultrasound spectra: a simulation study," IEEE Trans. Ultrason., Ferroelec. & Freq. Control, UFFC-33, pp. 747–753 (1986)) that the spectral power of any zero-mean Gaussian signal (including white noise) is governed by the exponential probability density distribution:

$$F_x(x) = \frac{1}{m} e^{\frac{x}{m}}, x \geq O \quad (1)$$

where the mean and standard deviation of x are given by:

$$E[x]m; \sigma=m \quad (2)$$

Figure 3:
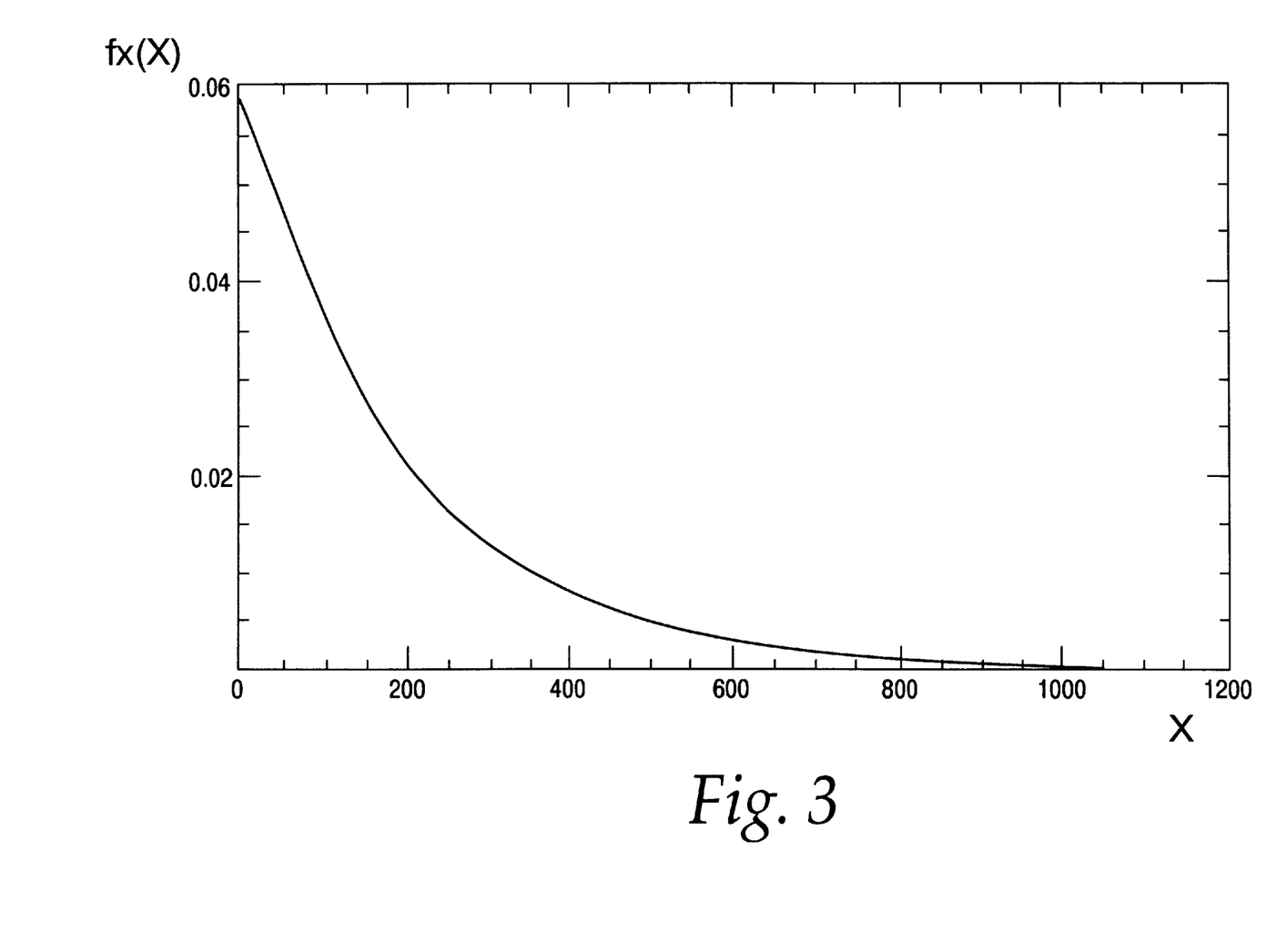
FIG. 3 is a graph showing the exponential probability density distribution. $F_x(x)$ for a mean value m=200.

For a digital Doppler system, x is typically a 12 to 16-bit integer. A plot of $f_x(x)$ versus x for m=200 is shown in FIG. 3.

The preferred embodiment of the present invention calculates a noise threshold which is a function of the mean noise level m of the signals resulting from the FFT power spectrum function (shown as X in FIG. 1) which can be estimated using a system noise model.

Alternatively, the noise threshold can be determined empirically by measuring noise at various system gain settings and preparing a table of values of noise versus gain. The table can be implemented as a look up table in host computer 24 which includes one or more logic units. When the gain changes by operator manipulation of control keys 26, the value of the noise threshold changes in accordance with the look up table. Alternatively, the look up table can be implemented in hardware.

It is assumed that the Doppler sample volume has already been positioned at the site of interest within the patient or subject under study S (FIG. 1), and that a clear spectral waveform has appeared on the display 18, except that the spectral waveform may be asymmetric about the baseline, inverted, aliased or has a frequency span much smaller than the current velocity scale. Instead of manually toggling a set of switches, the auto velocity scale PRF adjustment can be activated via a single button 26A. Alternatively, the spectral data in memory 22 can be periodically sampled to see if velocity scale and PRF adjustments are needed. Computer 24 then preferably executes the algorithm shown in FIG. 4 on the data arrangement shown in section B of FIG. 5.

Figure 4:
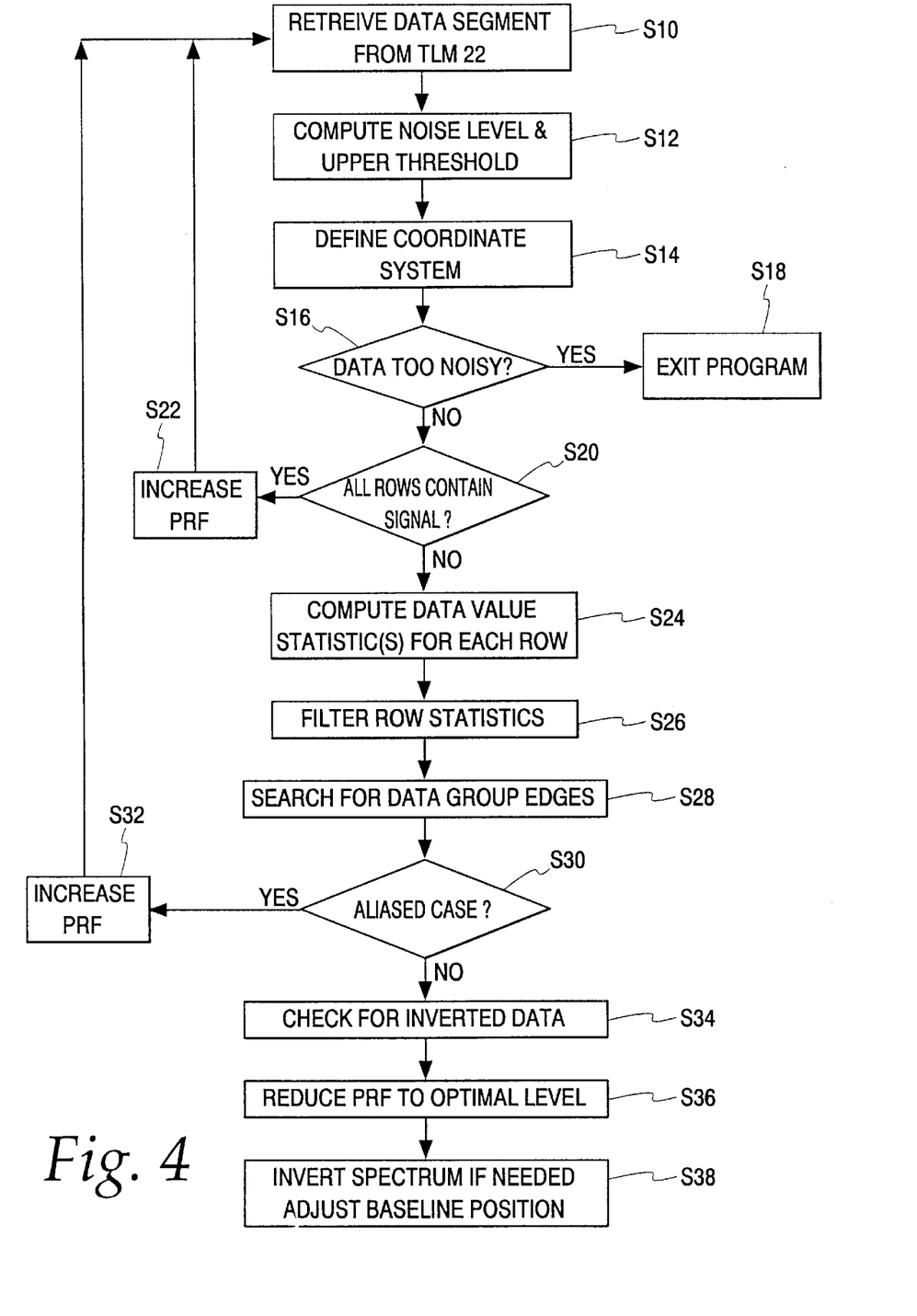
FIG. 4 is a flow diagram of a preferred form of algorithm in accordance with the invention.

According to step S10, the most recent image segment of N spectral lines that cover at least one complete cardiac cycle (i.e., time period CC shown in FIG. 2, e.g., 1.5 sec.), is retrieved from the memory 22. In general, N is a function of the time-line sweep speed which is user-adjustable via a front-panel 26 control key. For an 8-bit display, the spectrum intensity ranges from 0 to 255.

According to step S12, the preferred method for estimating the spectral noise floor or threshold assumes that the system noise originates primarily from the pre-amp in each receive channel in the beamformer 4 of a digital scanner. The pre-amp Johnson noise can be specified as a root-mean-square (RMS) voltage per Hz at room temperature 6. Thus, knowing the equivalent noise bandwidth of all the filters in the Doppler signal path (from receiver 4 to FFT processor function 12 in FIG. 1) enables an absolute RMS noise level to be computed as a function of system gain knob (user adjustable) on front panel 26. Any quantization noise due to analog-to-digital conversion also can be added in an appropriate manner. Further, knowing the sample volume position and aperture strategy in the Doppler mode, the total system noise can be computed by summing over all active receive channels (including array apodization effects) for a given sample volume position. Dividing this total noise level by the number of FFT points yields the mean spectral noise power m of the exponential distribution (Eqn. 1). Thus, by applying standard statistical transformations based on the known log compression function, the theoretical noise distribution in the TLM image segment can be obtained for a given mean spectral noise power.

The mean noise value in memory 22 can be computed by taking the first moment of the theoretical noise distribution. To determine a suitable upper noise threshold for signal detection, the $(1-\alpha)$th percentile point (e.g. $\alpha=0.01$) of the theoretical noise distribution can be used. An additional offset can be added to this to account for the limited accuracy of the system noise model.

Figure 5:
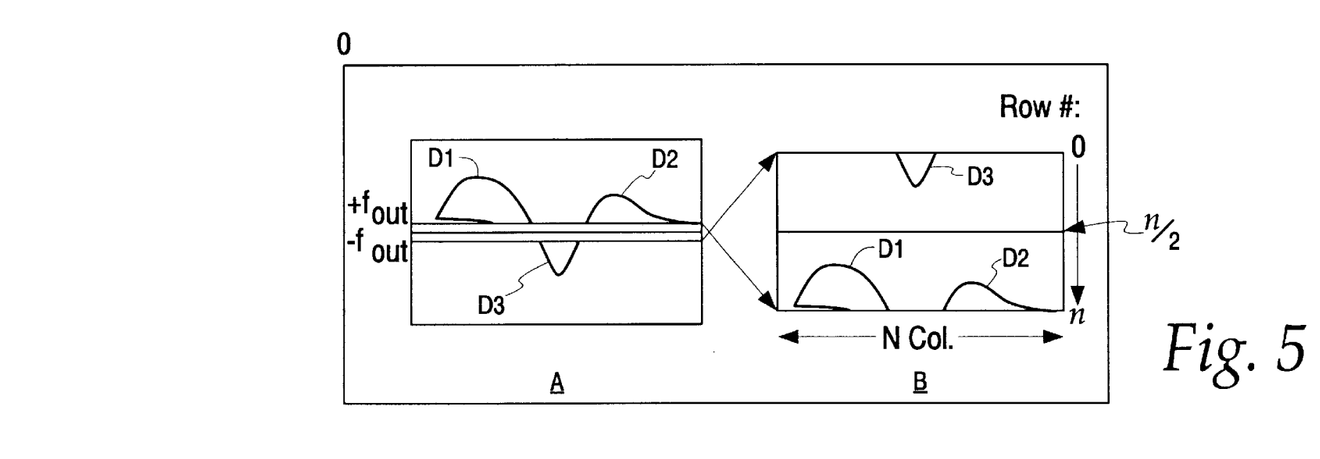
FIG. 5 is an illustration of data arrangements in a memory according to a preferred embodiment of the invention.

According to step S14, in order to describe and implement a spectrogram edge detection algorithm, a coordinate system needs to be specified. One exemplary coordinate system is to re-arrange the positive and negative frequency portions of the spectral data from memory 22 as shown in FIG. 5. Although other coordinate systems can support the same algorithm, the proposed coordinate system is convenient in that any aliased forward or reverse flow spectrum in the image is unfolded automatically for analysis. The wall signal rejection regions bounded by the negative $(-f_{cut})$ and positive $(f_{cut})$ cutoff points of wall filter function 10 are excluded. The rows from the top to bottom are numbered 0 to n. The columns are numbered 0-N. FIG. 5 represents memory locations addressable in o-n rows and 0-N columns. The memory locations store groups of signals D1 and D2 responsive to fluid flow in subject S in a first direction and signals D3 responsive to fluid flow in subject S in a second direction opposite the first direction.

Section A of FIG. 5 shows the arrangement of spectral data in memory 22 as will be displayed on the video monitor. Section B of FIG. 5 shows the arrangement of data in a memory of computer 24 after the coordinate system is specified. In general the zero frequency/velocity baseline in the spectral image may be shifted up or down, but in the example of Section A, the baseline is positioned at the middle of the frequency axis (i.e. no baseline shift), so that in Section B, row n/2 separates signals resulting from fluid flow in subject S in opposite directions. Fluid flow in a positive direction results in signals in rows n/2 to n; fluid flow in a negative direction results in signals in rows 0 to n/2. In addition, aliasing can cause signals indicating negative fluid flow even though they resulted from positive fluid flow and vice versa.

According to step S16, the first test is to check if the data contains pure noise only, or the signal is so weak that it will not be possible to perform a reliable edge detection. Since the theoretical noise distribution has been computed in Step S12, many simple threshold tests are possible. For example, of the N×n samples in the data, if the maximum signal value does not exceed the upper noise threshold by a minimum amount, and/or the mean data value over all the memory locations does not exceed the theoretical mean noise value by a minimum amount, then the data is considered to be "too noisy," and nothing needs to be done, and the program is exited in step S18.

Step S20 checks if all rows in the data contain signal (as opposed to noise). If so, the data bandwidth is equal to or larger than the current PRF, and the PRF should be increased. Some simple threshold tests can be used. For example, if fewer than approximately 5 rows have mean values less than the theoretical mean noise value, then the signal data is considered to have spanned the entire frequency axis. If this test proves positive, the PRF can be increased by a factor (e.g. two times) that may depend on the difference between the row with the highest mean intensity and that with the lowest mean intensity. If the difference is small, chances are higher that the spectrogram is wrapped around multiple times, in which case PRF should be increased in step S22 by a larger factor. The PRF is increased by having computer 24 send a signal to control 1A of transmitter 1 (FIG. 1).

After the PRF increase, the algorithm waits for a new spectral data segment (one second or more) to be generated in the TLM 22, and then repeats the above steps starting from Step S10. If the number of times PRF has been increased reaches some maximum limit (e.g. two times), or the PRF has already reached its maximum limit, but the data is still in "all signal" state, then the algorithm is exited.

According to step S24, the data value statistics are analyzed row by row, and a search is conducted for rows which show significant deviations from the predicted noise value statistics. Theoretically, the most comprehensive test is to compare a data value histogram for each row (or set of adjacent rows) against the theoretical noise distribution, based on standard histogram tests. The histogram plots data value versus number of occurrences for each row shown in section B of FIG. 5.

In practice, however, for N columns sufficiently large, some key statistical parameters that characterize the data value histogram for each row can be used to determine whether a row contains one or more signal values or only noise values. For example, if the mean value of a row exceeds the theoretical mean, the row contains one or more signal values. For another example, if the number of sample values which have exceeded the upper noise threshold value are greater than a minimum number, e.g. 3, the row contains one or more signal values. For a third example, the total intensity above noise threshold (TI) is computed where TI is defined as TI=Σ(Si−NT), for all Si greater than NT; where Si sample values; NT=upper noise threshold; and TI=total intensity above NT. If TI exceeds an empirically-determined signal threshold, for example, 5 db for the dynamic range setting in use, the row contains one or more signal values. The foregoing three examples also can be used in combination. Step S24 also identifies the widest group of adjacent rows of noise in the memory locations.

According to step S26, to reduce statistical variations for easier edge detection, a filter can be applied to the row statistic(s) over successive rows. A simple example is a smoothing filter which takes a moving average over, say, 5 rows. The filter in general does not have to be linear. For example, a median filter can be used to smooth the row statistic(s) while preserving edges.

If step S28 is reached, both signal and noise are present. FIGS. 6A–6D show arbitrary groups of signal data SD1–SD5 in the memory locations illustrated in section B of FIG. 5. The locations outside groups SD1–SD5 are noise or zero signal value. The data groups form boundaries B1–B10. As depicted in FIGS. 6A–6D, four cases are possible.

Step S28 finds the two edges of the memory signal data which will enable determination of optimal PRF and baseline position. An edge is defined as the outermost row in the signal data (as opposed to noise data) which exceeds a noise threshold value. The row numbers are indicated by Edge1 and Edge2 in each of the four cases in FIGS. 6A–6D.

The search for Edge1 and Edge2 is carried out in a sequential manner starting from row 0 down to row n. However, it is advantageous (but not required) to first identify the widest noise region in which the number of successive rows with mean signal values below the noise threshold is greatest. Using the case of FIG. 6B as an example, the widest noise region is that between Edge1 and Edge2. The widest noise region was determined in step S24.

Figure 6A:
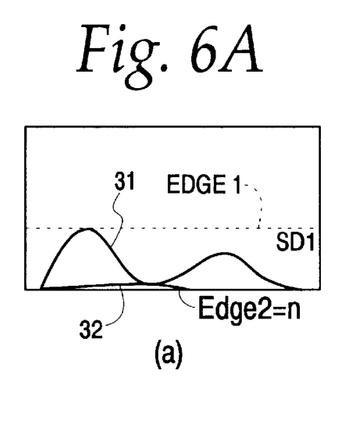
FIGS. 6A–6D are illustrations of arbitrary data arrangements in the memory illustrating the identification of portions of the data by the algorithm of FIG. 4.
Figure 6B:
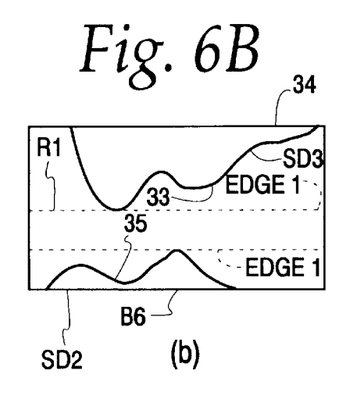

Starting from the middle row within the widest noise region, R1, a search is conducted in both directions (increasing and decreasing row numbers) for the first rows which exceed the noise threshold criterion. This avoids searching through the signal regions which may contain rows that happen (due to its statistical nature) to have low mean values.

In this edge detection process, the noise threshold criterion may be based on the first row whose mean signal value has exceeded the theoretical mean noise value (plus some offset), or the first row with more than a small number of data samples (e.g. 5) exceeding the upper noise threshold value calculated from Step S12, or the first row in which the total intensity above the noise threshold (TI) as calculated from step S24 is greater than an empirically-determined signal threshold, for example, 5 db for the dynamic range setting in use. The search locates a portion of boundaries B1–B10. To make this process more robust under poor signal-to-noise conditions, the edge detection criterion can require a few (e.g., 3–5) successive rows to have exceeded the noise threshold value.

Figure 6C:
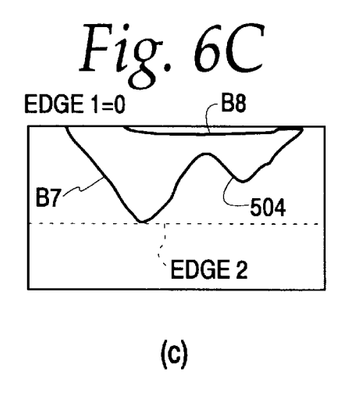
Figure 6D:
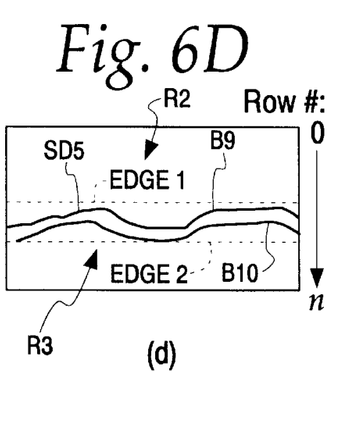

Of the four cases shown in FIGS. 6A–6D, the case of FIG. 6D (case (D)), is special in that neither Edge1 nor Edge2 is at or very near to row 0 or row n. Step S30 analyzes this case which can occur if a small sample volume in subject S is placed near the center of a large vein, for example. Case (D) is an ambiguous case: even though it is surrounded by clear noise regions R2 and R3, the signal data may have aliased to its present position. In this case, the PRF is increased to either a larger or the maximum possible PRF in step S32. Then steps starting from Step S10 are repeated. (As an option, steps S16, S18 and S20 can be skipped). If the edges (i.e., edges 1 and 2) of the data after the PRF increase remain the same in terms of absolute velocity units, then it is not aliased. If the edges have moved to other velocity positions, or if some of the locations of some of the signals at or near boundaries B9 and B10 have moved, the data must have been aliased before the PRF increase. In fact, it could still be aliased at maximum PRF, and a warning message should be displayed or a user of the system should otherwise be informed or signaled.

Once Edge1 and Edge2 are found, the widths of the positive (forward flow) and negative (reverse flow) frequency portions of the data (Section A of FIG. 5, before the coordinate defining operation of Step S14) are determined in step S34.

If the negative frequency width is larger than the positive frequency width, the signal data is considered to be inverted (i.e. the taller of the forward and reverse flow spectra is pointing downwards in the original data (Section A of FIG. 5)).

An auto invert flag is set to the "invert" state. The width can be determined by counting rows or subtracting row numbers identified by the edges identified by step S28. FIGS. 6B and 6C are examples of inverted groups of data signals. FIG. 6A is an example of noninverted data signals.

Having identified Edge1 and Edge2 as boundary rows of the data, the total row count for all memory locations corresponding to signals (as opposed to noise) is computed. This is converted into total velocity range or frequency bandwidth of the data based on the current velocity/frequency scale of display 18.

The optimal PRF is given by this data frequency bandwidth divided by a scale factor (e.g. 75%), which specifies the desired fraction of the total number of pixel rows of display 18 to be covered by the flow spectra (i.e., it is desirable to allow some margin between the upper edge of the spectrogram and the upper limit of the velocity scale). If the optimal PRF is not an available PRF setting, the new PRF can be set at the smallest PRF above the optimal PRF.

If the current PRF equals the new PRF, there is no need to reduce the PRF, and the algorithm proceeds to step S36.

If the current PRF is greater than the new PRF, the algorithm reduces the PRF to the new PRF, and updates the total spectrogram row number count on the positive and negative frequency axes of display 18 according to the PRF change factor.

The final step S38 in this algorithm is to effect the invert operation and the optimal baseline shift. If the auto invert flag (from Step S34) is negative (no need to invert), the optimal baseline position (from the bottom as shown in FIG.

2) corresponds to the row count of the negative frequency portion of the data plus some non-zero margin (e.g. 5 rows) to ensure that the spectrogram image of display 18 will not be touching the bottom of the display. Since the velocity scale typically consists of a number of tick marks, the baseline position can also be rounded up to match the nearest tick mark.

If the auto invert flag is positive (need to invert), the invert operation 32 (FIG. 1A) of function 12 (FIG. 1) is activated. In this case, the optimal baseline position is based on the row count of the positive portion of the signal spectrogram plus a small margin.

Figure 7:
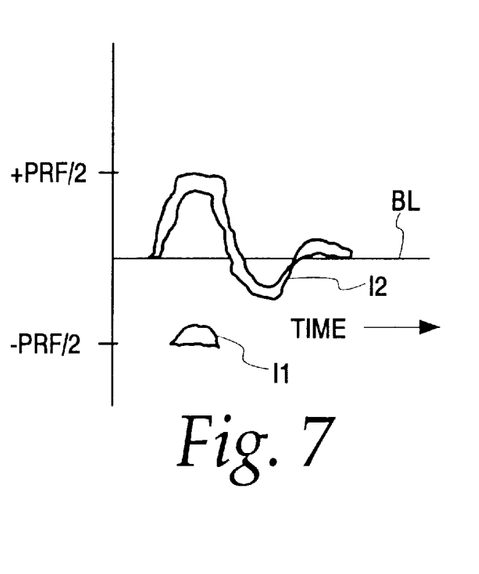
FIG. 7 is a graph showing a Doppler image resulting from aliasing.

FIG. 7 shows a typical Doppler image distorted by aliasing in which a group of images I1 appear in the negative flow portion of the display (below baseline BL which is set at zero frequency or velocity). Images I1 inaccurately indicate fluid flow in the negative direction. Images I2 also indicate fluid flow in the negative direction.

Figure 8:
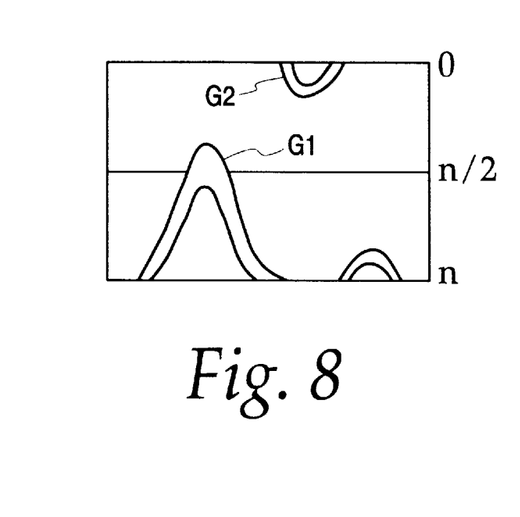
FIG. 8 is an illustration of the data arrangement in the memory resulting in the image of FIG. 7.
Figure 9:
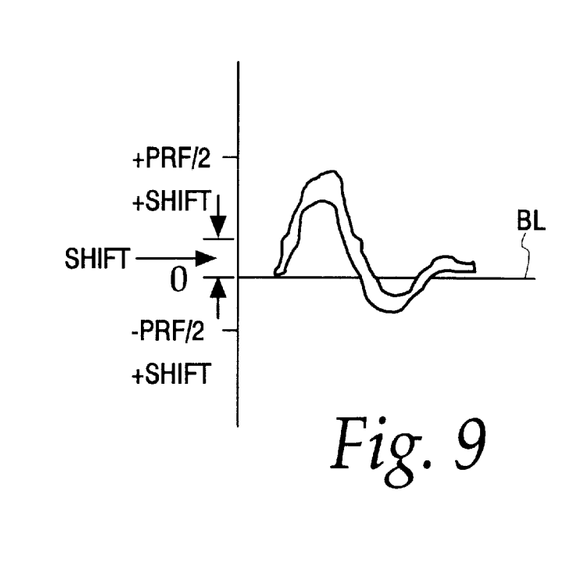
FIG. 9 is a graph showing the Doppler image resulting from operation of the algorithm of FIG. 4 on the data of FIG. 8.

FIG. 8 shows the signals in the memory locations of Section B of FIG. 5 which would result in the display shown in FIG. 7. Signal group G1 corresponds to image I1 and appears in the memory locations indicating negative flow (rows o-n/2). Signal group G2 corresponds to image I2. The algorithm counts the rows in group G2 and shifts baseline BL by a corresponding amount as shown in FIG. 9. Thus, images I1 and I2 are properly joined with the other signals indicating fluid flow in the positive direction.

The foregoing preferred embodiments have been disclosed for the purpose of illustration. Variations and modifications will be readily apparent to those skilled in the art. All such variations and modifications are intended to be encompassed by the claims set forth hereinafter. For example, processing blocks 12, 14 and 20 can be combined into a single processor.

What is claimed is:

1. In an ultrasound system comprising a Doppler spectrogram image display unit including a first control for controlling the polarity of a displayed Doppler image and a second control for shifting the position of the displayed Doppler image, apparatus for improving the appearance of the Doppler image comprising in combination:
   an ultrasound transmitter connected to transmit ultrasound waves at a predetermined pulse repetition frequency, the transmitter comprising a third control for adjusting the pulse repetition frequency;
   a receiver connected to generate Doppler signals in response to the ultrasound waves backscattered from a subject under study;
   a memory comprising memory locations connected to store memory signals having memory values, the memory signals including first signals having first values representing the magnitudes of at least some of the component frequencies of the Doppler signals generated over a predetermined time period in response to the backscattered ultrasound waves due to fluid flow in a first direction and second signals having second values representing the magnitudes of at least some of the component frequencies of the Doppler signals generated over the predetermined time period in response to the backscattered ultrasound waves due to fluid flow in a second direction opposite the first direction; and
   a logic unit connected to generate a third signal having a third value related to a noise signal level present in the system, to analyze the memory values based at least in part on the third value, and to enable adjustment of one or more of the first control, second control and third control in response to the analysis, whereby the Doppler image generated by the Doppler spectrogram image display unit is changed.

2. Apparatus, as claimed in claim 1, wherein the predetermined time period is at least one cardiac cycle.

3. Apparatus, as claimed in claim 1, wherein the noise signal level comprises at least an estimate of a mean noise intensity level.

4. Apparatus, as claimed in claim 3, wherein the mean noise intensity level comprises at least an estimate of the mean noise intensity level in the first and second signals.

5. Apparatus, as claimed in claim 3, wherein the logic unit is connected to generate the third signal based on system noise including preamplifier Johnson noise.

6. Apparatus, as claimed in claim 1, wherein the logic unit comprises a Fourier transform algorithm.

7. Apparatus, as claimed in claim 1, wherein the memory is addressable in columns and rows and wherein the logic unit is connected to enable a change in the second control resulting in an increase in the pulse repetition rate if substantially all rows in the memory locations contain a memory value having a predetermined relationship with respect to the third value.

8. Apparatus, as claimed in claim 1, wherein the logic unit is connected to determine whether there are more rows storing first signals or second signals and is connected to enable a change in the first control in response to the determination enabling a change in the position of the Doppler image.

9. Apparatus, as claimed in claim 8, wherein the change of position is an inversion.

10. Apparatus, as claimed in claim 1, wherein the logic unit is connected to count the numbers of rows storing signals indicating flow in the second direction and to enable the second control to shift the image by an amount related to the row count.

11. Apparatus, as claimed in claim 1, wherein the logic unit is connected to count the number of rows storing the first and second signals and for enabling the third control to adjust the pulse repetition frequency to a frequency related to the counted number of rows.

12. Apparatus, as claimed in claim 1, wherein the logic unit is connected to identify a pattern of memory signals in which the rows storing the first and second signals are located between rows in which first and second signals are absent, to determine the locations of at least some of the first and second signals adjacent locations in which first and second signals are absent, to enable the third control to increase the pulse repetition rate, and to enable the signaling of a user if at least some of the locations have moved in response to the increase of the pulse repetition rate.

13. Apparatus, as claimed in claim 1, wherein the logic unit is connected to generate statistics for at least one row of the memory locations.

14. Apparatus, as claimed in claim 1, wherein the receiver comprises a wall filter connected to filter a band of component frequencies of the ultrasound waves backscattered form the subject and wherein the logic unit is connected to eliminate from the memory locations rows corresponding to the band of component frequencies.

15. Apparatus, as claimed in claim 1, wherein the memory is addressable in columns and rows and wherein the logic unit is connected to analyze the memory values by summing the memory values in at least one row which exceed the third value to generate a summed value and comparing a value related to the summed value to an empirically-determined value.

16. In an ultrasound system comprising a Doppler image display unit for displaying a Doppler image with an adjustable polarity and an adjustable position, a method of improving the appearance of the Doppler image comprising the steps of:

transmitting ultrasound waves at a predetermined pulse repetition frequency;

generating Doppler signals in response to the ultrasound waves backscattered from a subject under study;

storing memory signals having memory values, the memory signals including first signals having first values representing the magnitudes of at least some of the component frequencies of the Doppler signals generated over a predetermined time period in response to the backscattered ultrasound waves due to fluid flow in a first direction and second signals having second values representing the magnitudes of at least some of the component frequencies of the Doppler signals generated over the predetermined time period in response to the backscattered ultrasound waves due to fluid flow in a second direction opposite the first direction;

generating a third signal having a third value related to a noise intensity level present in the system;

analyzing the memory values based at least in part on the third value; and adjusting one or more of the polarity, position and pulse repetition rate in response to the analyzing, whereby the Doppler image generated by the Doppler image display unit is changed.

17. A method, as claimed in claim 16, wherein the predetermined time period is at least one cardiac cycle.

18. A method, as claimed in claim 16, wherein the noise signal level comprises at least an estimate of a mean noise intensity level.

19. A method, as claimed in claim 18, wherein the mean noise intensity level comprises at least an estimate of the mean noise intensity level in the first and second signals.

20. A method, as claimed in claim 18, wherein the step of generating the third signal comprises the step of estimating the total system noise including preamplifier Johnson noise.

21. A method, as claimed in claim 16, wherein the step of analyzing comprises the step of performing a Fourier transform.

22. A method, as claimed in claim 16, wherein the step of storing comprises the step of storing in columns and rows and wherein the step of adjusting comprises the step of increasing the pulse repetition rate if substantially all rows in the memory locations contain a memory value having a predetermined relationship with respect to the third value.

23. A method, as claimed in claim 16, wherein the step of analyzing comprises the step of determining whether there are more rows storing first signals or second signals and wherein the step of adjusting comprises the step of changing the polarity in response to the determination enabling a change in the position of the Doppler image.

24. A method, as claimed in claim 23, wherein the change of position is an inversion.

25. A method, as claimed in claim 16, wherein the step of analyzing comprises the step of counting the rows storing signals indicating fluid flow in the second direction and wherein the step of adjusting comprises the step of shifting the image by an amount related to the result of the row counting.

26. A method, as claimed in claim 16, wherein the step of analyzing comprises the step of counting the rows storing the first and second signals and wherein the step of adjusting comprises the step of adjusting the pulse repetition frequency to a frequency related to the result of the row counting.

27. A method, as claimed in claim 16, wherein the step of analyzing comprises the steps of:

identifying a pattern of memory signals in which the rows storing the first and second signals are located between rows in which first and second signals are absent;

determining the locations of at least some of the first and second signals adjacent locations in which first and second signals are absent; and increasing the pulse repetition rate;

and wherein the step of adjusting comprises the step of enabling the signaling of a user if at least some of the locations have moved in response to the increase of the pulse repetition rate.

28. A method, as claimed in claim 16, wherein the step of analyzing comprises the step of generating statistics for at least one row of the memory locations.

29. A method, as claimed in claim 16, wherein the step of receiving comprises the step of wall filtering a band of component frequencies of the ultrasound waves backscattered from the subject and wherein the step of analyzing comprises the step of eliminating from the memory locations rows corresponding to the band of component frequencies.

30. A method, as claimed in claim 16, wherein the step of storing comprises the step of storing in columns and rows and wherein the step of analyzing the memory values comprises the step of summing the memory values in at least one row which exceed the third value to generate a summed value and comparing a value related to the summed value to an empirically-determined value.

* * * * *